(12) United States Patent
Bron

(10) Patent No.: US 6,957,568 B2
(45) Date of Patent: Oct. 25, 2005

(54) SMALL PARTICLE IMPINGEMENT COMPARATOR AND METHOD OF DETERMINING NUMERICAL ESTIMATION OF A STEAM PATH COMPONENT SURFACE ROUGHNESS

(75) Inventor: Chris R. Bron, Springfield, IL (US)

(73) Assignee: General Electric Company, Schenectady, NY (US)

( * ) Notice: Subject to any disclaimer, the term of this patent is extended or adjusted under 35 U.S.C. 154(b) by 319 days.

(21) Appl. No.: 10/176,371

(22) Filed: Jun. 21, 2002

(65) Prior Publication Data

US 2003/0234650 A1    Dec. 25, 2003

(51) Int. Cl.$^7$ ................................. G01B 5/28
(52) U.S. Cl. ............................ 73/105; 73/1.89
(58) Field of Search .................. 73/105, 1.89, 11.02

(56) References Cited

U.S. PATENT DOCUMENTS

| | | | |
|---|---|---|---|
| 2,715,830 A | * | 8/1955 | Lewis et al. .................. 73/1.89 |
| 3,505,861 A | * | 4/1970 | Schoefer et al. .............. 73/105 |
| 4,107,525 A | | 8/1978 | Hart, Jr. |
| 4,197,456 A | | 4/1980 | Fleischer et al. |
| 6,207,295 B1 | | 3/2001 | Stowell et al. |

OTHER PUBLICATIONS

GAR Electroforming Division, Electroformers Inc. Miscellaneous Disclosures from Website www.garelectroforming.com, 32 pages, printed out on Jun. 5, 2003, origination date unknown.
GE Power Generation Services Steam Turbine Photo Reference Guide, ES-STM-D6.2 Rev. 2 (May 1984), pp. 7 and 8.
Sanders, W.P., "Erosion Classification, Scales of Comparison and Means of Reporting Damage", 1975, pp. 1-13.

* cited by examiner

Primary Examiner—Robert Raevis
(74) Attorney, Agent, or Firm—Nixon & Vanderhye P.C.

(57) ABSTRACT

A small particle impingement comparator for surface finishes in excess of 1000 micro-inches standardizes the evaluation of such surface finishes within a turbine steam path. The small particle impingement comparator includes a plurality of sample cells arranged side-by-side in ascending order of roughness from 1190 micro-inches to 6950 micro-inches. With this comparator, users can compare the steam path component surface roughness with the roughness of the plurality of sample cells using a visual and tactile feel comparison.

10 Claims, 2 Drawing Sheets

SMALL PARTICLE IMPINGEMENT COMPARATOR AND METHOD OF DETERMINING NUMERICAL ESTIMATION OF A STEAM PATH COMPONENT SURFACE ROUGHNESS

BACKGROUND OF THE INVENTION

The present invention relates to performance evaluation of a steam turbine steam path and, more particularly, to a steam path small particle impingement surface finish comparator for determining a numerical estimation of a steam path component surface roughness in micro-inches.

During the execution of a performance evaluation of a steam turbine steam path, the surface finish of both the diaphragm nozzles and the rotor bucket vanes is a significant factor for the determination of performance losses. Measurement of the surface finish is currently performed by using a portable electronic profilemeter and commercially available shot peen and grit blast comparator gauges. Neither of these methods, however, is applicable for surface roughness above 1000 micro-inches. The unique surface finishes produced in the turbine steam path by Small Particle Impingement (SPI) is typically in excess of 1000 micro-inches, and at present, there is no comparator available that replicates this SPI impact finish. The development of an SPI comparator for surface finishes in excess of 1000 micro-inches will serve to standardize the evaluation of SPI surface finishes within the turbine steam path.

BRIEF DESCRIPTION OF THE INVENTION

In an exemplary embodiment of the invention, a small particle impingement comparator includes a plurality of sample cells arranged side-by-side in ascending order of roughness from 1190 micro-inches to 6950 micro-inches. In another exemplary embodiment of the invention, the small particle impingement comparator includes ten sample cells arranged in ascending order of roughness and having roughness values exceeding 1000 micro-inches. In still another exemplary embodiment of the invention, a method of determining a numerical estimation of a steam path component surface roughness in micro-inches, root mean squared, includes the steps of forming a plurality of sample cells in ascending order of roughness from 1190 micro-inches to 6950 micro-inches, and comparing the steam path component surface roughness with the roughness of the plurality of sample cells using a visual and tactile feel comparison.

DETAILED DESCRIPTION OF THE INVENTION

Figure 1:
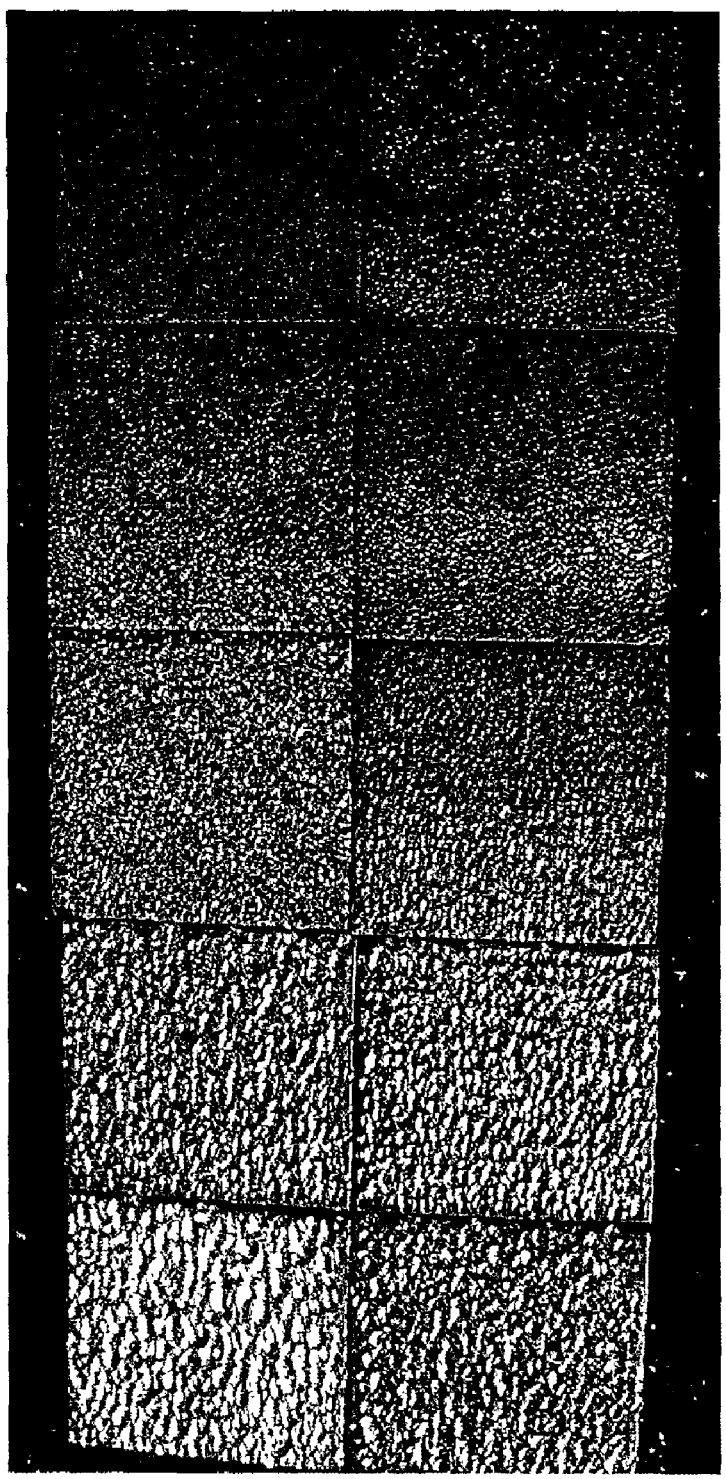
FIG. 1 shows master samples of small particle impingement ranging from 1190 to 6950 micro-inches.
Figure 2:
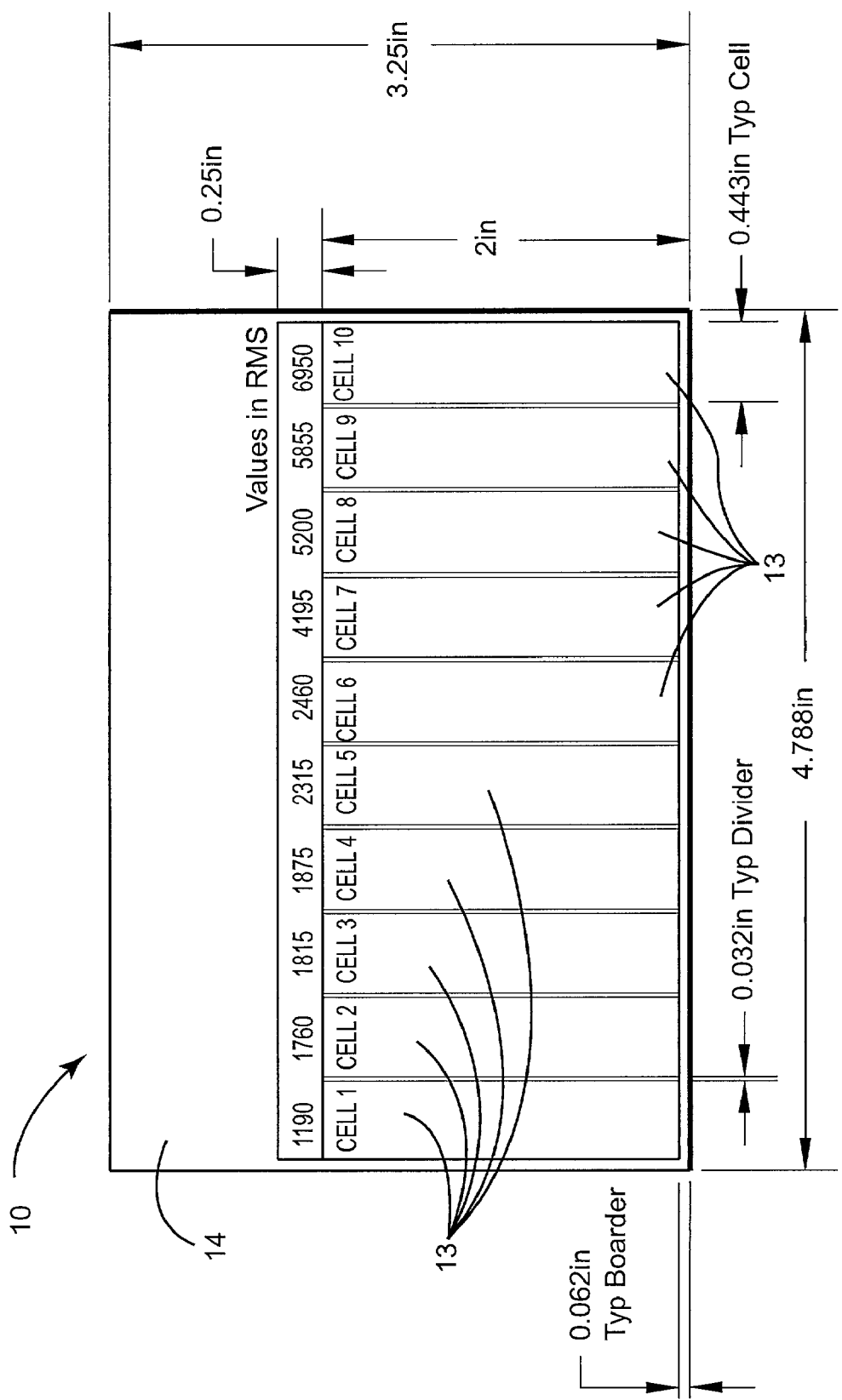
FIG. 2 is a schematic illustration of the small particle impingement comparator.

With reference to FIGS. 1 and 2, an SPI comparator 10 is developed using a plurality of master sample blocks 12. Preferably, ten master sample blocks 12 are used. A graphical representation of the ten master sample blocks 12 is shown in FIG. 1. The blocks 12 replicate typical surface conditions encountered in steam turbines. To form the comparator 10, the blocks 12 are machined to predetermined sizes and mounted in a brass frame, upon which letter graphics are engraved. This master assembly is then replicated using positive/negative transfers to arrive at the finished product. The final product is preferably made of electroformed nickel metal, although other materials may be suitable for the described application. The specific manufacturing process is known, for example by GAR Electroforming Division, Electroformers Inc. of Danbury, Conn., and does not form part of the invention. Further details thereof will thus not be described.

As shown, the comparator 10 includes a plurality of sample cells 13 arranged side-by-side in ascending order of roughness from 1190 micro-inches to 6950 micro-inches having preset roughness values. Using ten master sample blocks 12 to derive ten cells 13, the respective preset roughness values, as shown in FIG. 2, are preferably 1190, 1760, 1815, 1875, 2315, 2460, 4195, 5200, 5855, and 6950 micro-inches.

Dimensionally, the SPI comparator 10 is similar in size and portability to commercially available comparators in that it is generally pocket size in dimension (e.g., up to about 6"×8") and easily used to determine surface finish due to SPI for values above 1000 micro-inches. Exemplary dimensions of the SPI comparator 10 are shown in FIG. 2, although the invention is not meant to be limited to the illustrated dimensions. As shown, preferred exterior dimensions for an outer area 14 are 4.788 inches wide by 3.25 inches high. Each of the cells 13 is about two inches in length and 0.437 inches in width. Additional spaces and dimensions as shown in FIG. 2 are provided for an appropriate header, borders and dividers. Additionally, the comparator 10 is approximately 0.045 inches thick.

In operation, the SPI comparator 10 can be used to improve internal productivity and to better estimate the performance loss of rough surface finish conditions in excess of 1000 micro-inches. The user utilizes the SPI comparator 10 by visual and tactile feel comparison of the steam path surface finish with the replicated surface finishes contained in the cells 13 of the SPI comparator 10. The numerical values associated with each cell sample 13 allow for the numerical estimation of the steam path component surface roughness in micro-inches, root mean squared (RMS). The numerical values derived from the comparator 10 are used to calculate the thermodynamic performance loss of the steam path nozzle and/or bucket vane component for input into an analysis program.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A small particle impingement comparator comprising a plurality of sample cells arranged side-by-side in ascending order of roughness from 1190 micro-inches to 6950 micro-inches, the sample cells comprising surface patterns that replicate surface conditions as if produced via small particle impingement.

2. A small particle impingement comparator according to claim 1, comprising ten sample cells.

3. A small particle impingement comparator according to claim 2, wherein the ten sample cells have respective preset roughness values.

4. A small particle impingement comparator according to claim 3, wherein the preset roughness values from a first cell to a last cell are 1190 micro-inches, 1760 micro-inches, 1815 micro-inches, 1875 micro-inches, 2315 micro-inches, 2460 micro-inches, 4195 micro-inches, 5200 micro-inches, 5855 micro-inches, and 6950 micro-inches.

5. A small particle impingement comparator according to claim 1, the comparator being formed of electroformed nickel metal.

6. A small particle impingement comparator according to claim 5, comprising a thickness of about 0.045 inches.

7. A small particle impingement comparator according to claim 1, the comparator being formed in a pocket size.

8. A small particle impingement comparator comprising ten sample cells arranged in ascending order of roughness and having roughness values exceeding 1000 micro-inches, the sample cells comprising surface patterns that replicate surface conditions as if produced via small particle impingement.

9. A small particle impingement comparator according to claim 8, wherein the roughness values are preset between 1190 micro-inches to 6950 micro-inches.

10. A method of determining a numerical estimation of a steam path component surface roughness in micro-inches, root mean squared, the method comprising:

forming a plurality of sample cells in ascending order of roughness from 1190 micro-inches to 6950 micro-inches, the sample cells comprising surface patterns that replicate surface conditions as if produced via small particle impingement; and comparing the steam path component surface roughness with the roughness of the plurality of sample cells using a visual and tactile feel comparison.

* * * * *